United States Patent [19]

Fortunak et al.

[11] Patent Number: 6,049,019

[45] Date of Patent: Apr. 11, 2000

[54] PROCESS FOR THE PREPARATION OF CYCLOPROPYLACETYLENE

[75] Inventors: Joseph M. Fortunak, Newark; Zhe Wang; Jianguo Yin, both of Hockessin, all of Del.

[73] Assignee: DuPont Pharmaceuticals, Wilmington, Del.

[21] Appl. No.: 09/126,582

[22] Filed: Jul. 30, 1998

Related U.S. Application Data

[60] Provisional application No. 60/054,402, Jul. 31, 1997.

[51] Int. Cl.[7] .............................. C07C 2/02; C07C 2/00; C07C 1/207; C07C 69/74; C07C 61/04

[52] U.S. Cl. ......................... 585/538; 585/534; 585/359; 560/124; 562/506

[58] Field of Search ........................... 560/124; 562/506; 585/534, 538, 359

[56] References Cited

U.S. PATENT DOCUMENTS

| | | | |
|---|---|---|---|
| 5,250,540 | 10/1993 | Arlt et al. | 514/302 |
| 5,318,988 | 6/1994 | Schohe-Loop et al. | 514/458 |
| 5,407,599 | 4/1995 | de Meijere et al. | 252/299.01 |
| 5,468,882 | 11/1995 | Schohe-Loop et al. | 549/407 |
| 5,955,627 | 9/1999 | Nakazawa et al. | 560/124 |

FOREIGN PATENT DOCUMENTS

| | | |
|---|---|---|
| 0847974 | 6/1998 | European Pat. Off. . |
| WO9622955 | 8/1996 | WIPO . |

OTHER PUBLICATIONS

Thompson et al., Tetrahedron Letters, 1995, 36, No. 49, p. 8937–8940.

Carl Bernard Ziegler, Jr., Synthesis and Mechanistic Studies of Polyunsaturated Fatty Acid Hydroperoxides Involving a Novel Vinylcyclopropyl Bromide Ring, Ph.D. Dissertation, Duke University (1981) 139 pp.

*Primary Examiner*—Walter D. Griffin
*Assistant Examiner*—Tam M. Nguyen
*Attorney, Agent, or Firm*—Scott K Larsen

[57] ABSTRACT

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor. In the process, cyclopropane carboxaldehyde is condensed with malonic acid to form 3-cyclopropylacrylic acid; 3-cyclopropylacrylic acid is halogenated to form (E,Z)-1-halo-2-cyclopropylethylene; and (E,Z)-1-halo-2-cyclopropylethylene is dehydrohalogenated to form cyclopropyl acetylene. This improvement provides for high conversion of inexpensive, readily available starting materials into cyclopropylacetylene, high overall yields and can be conducted on an industrial scale.

13 Claims, No Drawings

PROCESS FOR THE PREPARATION OF CYCLOPROPYLACETYLENE

This application claims the benefit of U.S. Provisional Application No. 60/054,402, filed Jul. 31, 1997.

FIELD OF THE INVENTION

The present invention relates generally to novel methods for the synthesis of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI):

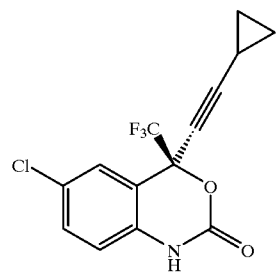

(VI)

is not only a highly potent reverse transcriptase inhibitor, it is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, economical and efficient synthetic processes for its production need to be developed.

Cyclopropylacetylene is an important reagent in the synthesis of compound (VI). Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown below. As a reagent the cyclopropylacetylene was synthesized in a 65% yield by cyclization of 5-chloropentyne with n-butyllithium at 0°–80° C. in cyclohexane followed by quenching with ammonium chloride. The process generates a low yield of cyclopropylacetylene which is not feasible for the large commercial process of a difficult to handle reagent.

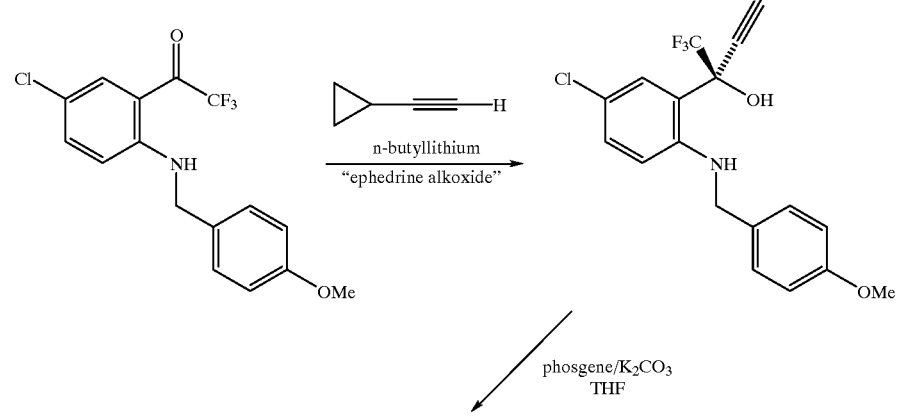

-continued

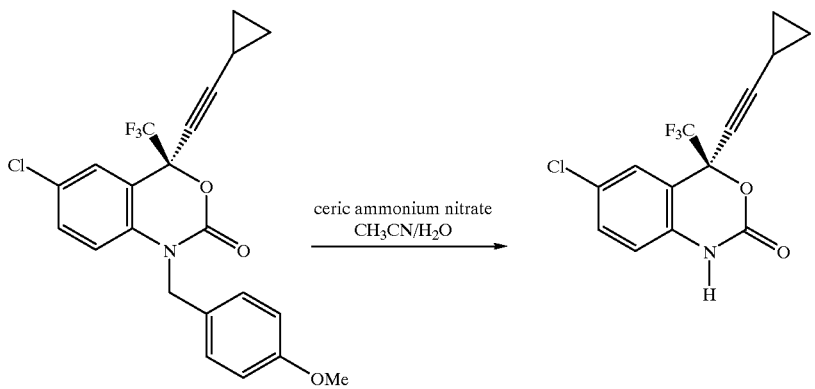

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3,1-benzoxazin-2-one. Application Wo 9622955 A1 discloses methods which continue to be inefficient in the overall synthesis on a kilogram scale for which this invention makes significant improvements.

The chemical literature shows the majority of the cyclopropylacetylene preparations involve the conversion of cyclopropylmethyl ketone to cyclopropyl-acetylene via the following chemical scheme. The method will produce cyclopropylacetylene on small scale, <1 kilogram, but is not amenable for bulk production, thus an alternative was developed.

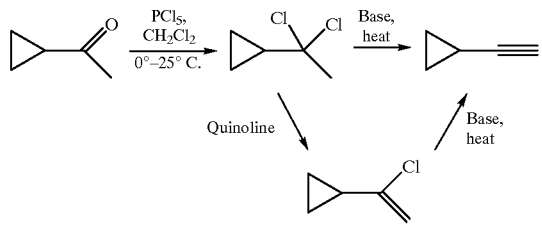

The above methods for the synthesis of cyclopropylacetylene use combinations of toxic, difficult to handle reagents, relatively expensive materials, incomplete conversions and low yields which render the overall synthesis inefficient and yield cyclopropylacetylene of lower purity. Thus, it is desirable to discover new synthetic routes to cyclopropylacetylene on a large scale which improve upon these limitations and provide high yields of desired cyclopropylacetylene.

The present invention discloses novel compounds and a novel scalable procedure for the preparation of cyclopropyl acetylene. Improvements over previously disclosed preparations of cyclopropyl acetylene are in the low economic rice and availability of the starting materials; the convenience and high yields for the chemistry; and the ability to crystallize and store without degradation the first intermediate, 3-cyclopropyl acrylic acid. The invention provides novel chemistry for the production of cyclopropyl acetylene from cyclopropane carboxaldehyde. The process provides a high yield (>90%) for the convenient reaction of cyclopropane carboxaldehyde with malonic acid to give 3-cyclopropyl acrylic acid. The subsequent transformation of 3-cyclopropyl acrylic acid to cyclopropyl vinyl halides occurs in high yield using convenient reaction conditions.

The final preparation of cyclopropyl acetylene by dehydrohalogenation from cyclopropyl vinyl halide proceeds in high yields and with suitable purities so that the cyclopropyl acetylene produced can be stored or used as a solution in an inert solvent.

None of the above-cited references describe the methods of the present invention for the synthesis of cyclopropylacetylene.

SUMMARY OF THE INVENTION

The present invention concerns an improved process suitable for the large scale preparation of cyclopropylacetylene. In the process, cyclopropane carboxaldehyde is condensed with malonic acid to form 3-cyclopropylacrylic acid; 3-cyclopropylacrylic acid is halogenated to form (E,Z)-1-halo-2-cyclopropylethylene; and (E,Z)-1-halo-2-cyclopropylethylene is dehydrohalogenated to form cyclopropyl acetylene. This improvement provides for high conversion of inexpensive, readily available starting materials into cyclopropylacetylene, high overall yields and can be conducted on an industrial scale.

DETAILED DESCRIPTION OF THE INVENTION

In a first embodiment, the present invention provides a process for the preparation of cyclopropylacetylene comprising:

(1) contacting cyclopropane carboxaldehyde with malonic acid, or a malonic acid substitute, in the presence of a base catalyst to form 3-cyclopropylacrylic acid, (2) contacting 3-cyclopropylacrylic acid with a metal 5 catalyst and a halogenating agent to form (E,Z)-1-halo-2-cyclopropylethylene; and (3) contacting (E,Z)-1-halo-2-cyclopropylethylene with a strong base to form cyclopropyl acetylene.

In a preferred embodiment, the present invention provides a process for the preparation of cyclopropylacetylene wherein the malonic acid substitute is selected from 2,2-dimethyl-1,3-dioxane-4,6-dione, dimethyl malonate, diethyl malonate, and monomethyl malonate.

In another preferred embodiment, the present invention provides a process for the preparation of cyclopropylacetylene wherein the base catalyst is selected from pyridine, pyrrolidine, piperidine, morpholine, N-methylmorpholine, 1,4-diazabicyclo[2.2.2]octane, N,N-dimethylaminopyridine, N,N-diethylaniline, quinoline, N,N-diisopropylethylamine, sodium hydroxide, potassium hydroxide, lithium hydroxide, cesium hydroxide, sodium carbonate, potassium carbonate, lithium carbonate, cesium carbonate, sodium alkoxide, lithium alkoxide and potassium alkoxide, wherein the alkoxide is selected from methoxide, ethoxide, butoxide, t-butoxide, and t-amyloxide.

In another preferred embodiment, the present invention provides a process for the preparation of cyclopropylacetylene wherein the metal catalyst is selected from lithium acetate, magnesium acetate, zinc acetate, calcium acetate, copper iodide and copper bromide.

In another preferred embodiment, the present invention provides a process for the preparation of cyclopropylacetylene wherein the halogenating agent is selected from N-chlorosuccinimide, N-bromosuccinimide, and N-iodosuccinimide.

In a further preferred embodiment, the present invention provides a process for the preparation of cyclopropylacetylene comprising:

(1) contacting cyclopropane carboxaldehyde with malonic acid in the presence of a base catalyst selected from:

pyridine, pyrrolidine, piperidine, morpholine, N-methylmorpholine, 1,4-diazabicyclo[2.2.2]octane, N,N-dimethylaminopyridine, N,N-diethylaniline, quinoline, N,N-diisopropylethylamine, sodium hydroxide, potassium hydroxide, lithium hydroxide, cesium hydroxide, sodium carbonate, potassium carbonate, lithium carbonate, cesium carbonate, sodium alkoxide, lithium alkoxide and potassium alkoxide, wherein the alkoxide is selected from methoxide, ethoxide, butoxide, t-butoxide, and t-amyloxide; to form 3-cyclopropylacrylic acid;

(2) contacting 3-cyclopropylacrylic acid with a metal catalyst selected from:
lithium acetate, magnesium acetate, zinc acetate, calcium acetate, copper iodide and copper bromide;
and a halogenating agent to form (E,Z)-1-halo-2-cyclopropylethylene; and (3) contacting (E,Z)-1-halo-2-cyclopropylethylene with methyllithium, potassium t-butoxide, potassium hydroxide, or sodium amide to form cyclopropyl acetylene.

In an even further preferred embodiment, the present invention provides a process for the preparation of cyclopropyl-acetylene comprising:

(1) contacting cyclopropane carboxaldehyde with malonic acid in the presence of a base catalyst selected from:
pyridine, pyrrolidine, piperidine, morpholine, or a combination thereof;
to form 3-cyclopropylacrylic acid;

(2) contacting 3-cyclopropylacrylic acid with a metal catalyst selected from:
lithium acetate, magnesium acetate, zinc acetate, calcium acetate, copper iodide and copper bromide;
and a halogenating agent to form (E,Z)-1-halo-2-cyclopropylethylene; and (3) contacting (E,Z)-1-halo-2-cyclopropylethylene with potassium t-butoxide, potassium hydroxide, or sodium amide to form cyclopropyl acetylene.

In yet an even further preferred embodiment, the present invention provides a process for the preparation of cyclopropyl-acetylene comprising:

(1) contacting cyclopropane carboxaldehyde with malonic acid in the presence of a base catalyst selected from:
pyridine, pyrrolidine, piperidine, morpholine, or a combination thereof;
to form 3-cyclopropylacrylic acid;

(2) contacting 3-cyclopropylacrylic acid with lithium acetate and a halogenating agent to form (E,Z)-1-halo-2-cyclopropylethylene; and (3) contacting (E,Z)-1-halo-2-cyclopropylethylene with methyllithium, potassium t-butoxide, potassium hydroxide, or sodium amide to form cyclopropyl acetylene.

In a most preferred embodiment the halogenating agent is N-bromosuccinimide.

In a second embodiment, the present invention provides a process for the preparation of cyclopropylacetylene comprising in step (2) contacting 3-cyclopropylacrylic acid with a metal catalyst and a halogenating agent in the presence of a phase transfer agent to form (E,Z)-1-halo-2-cyclopropylethylene.

In a third embodiment, the present invention provides a process for the preparation of cyclopropylacetylene comprising in step (3) contacting (E,Z)-1-halo-2-cyclopropylethylene with a strong base in the presence of a phase transfer agent to form cyclopropyl acetylene.

In a fourth embodiment, the present invention provides a compound of formula $C_3H_5CH=CHBr$.

In a fifth embodiment, the present invention provides a compound of formula $C_3H_5CH=CHCl$.

The processes of the present invention are useful for the preparation cyclopropylacetylene, an essential intermediate in the synthesis of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor, and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature, unless the purpose of the solvent is to quench the reaction. A given reaction may be carried out in one solvent or a mixture of more than one solvent. Depending on the particular reaction step, suitable solvents for a particular reaction step may be selected independent of any other reaction step.

Suitable halogenated solvents include chlorobenzene, dichloromethane, chloroform, carbon tetrachloride, dichlorobenzene, dichloroethane, and trichloroethane.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, anisole, or t-butylmethyl ether.

Suitable hydrocarbon or aromatic solvents include: benzene, cyclohexane, pentane, hexane, toluene, cycloheptane, methylcyclohexane, heptane, ethylbenzene, m-xylene, o-xylene, p-xylene, octane, indane, nonane, naphthalene and mesitylene(s).

As used herein, the term "base catalyst" refers to any agent which catalyzes the condensation of malonic acid with the carbonyl carbon of cyclopropyl carboxaldehyde thus effecting the formation of cyclopropyl acrylic acid. Examples of base catalysts include, but are not limited to, alkylamines and aromatic amines such as: pyridine, pyrrolidine, piperidine, morpholine, N-methylmorpholine, 1,4-diazabicyclo[2.2.2]octane (DABCO), N,N-diethylaniline, N,N-dimethylaminopyridine(s), quinoline, and N,N-diisopropylethylamine; as well as sodium, potassium, lithium or cesium hydroxide; sodium, potassium, lithium or cesium carbonate; and alkoxide bases such as sodium, lithium or potassium methoxides, ethoxides, butoxides, t-butoxides, and t-amyloxides.

As used herein, the term "metal catalyst" refers to any agent which catalyzes the decarboxylation and subsequent halogenation of cyclopropyl acrylic acid by a halogenating agent in step (2) to effect the formation of an (E,Z) mixture of 1-halo-2-cyclopropylethylene. Examples of metal catalysts include, but are not limited to, sodium carbamate, potassium carbamate, lithium carbamate, copper bromide, and metal acetates, including but not limited to, lithium acetate, magnesium acetate, zinc acetate, and calcium acetate.

As used herein, the term "halogenating agent" refers to any agent which under the conditions of step (2) effects halogenation of cyclopropyl acrylic acid in the presence of a base catalyst to effect formation of an (E,Z) mixture of 1-halo-2-cyclopropylethylene. Examples of halogenating agents include, but are not limited to, N-bromosuccinimide, N-chlorosuccinimide, N-iodosuccinimide, $Br_2$, $Cl_2$, triphenylphosphine dibromide, and triphenylphosphine dichloride.

As used herein, the term "strong base" refers to any base the presence of which in the reaction facilitates the synthesis of cyclopropyl acetylene from 1-halo-2-cyclopropylethylene. Suitable bases may be selected by one of skill in the art of organic synthesis. Suitable bases include, but are not limited to, inorganic bases such as alkali metal, alkali earth metal, and ammonium hydroxides and alkoxides. Suitable bases also include, but are not limited to, metal amides and alkyl lithiums. Examples of suitable strong bases are lithium diisopropyl amide, sodium amide, sodium methoxide, potassium t-butoxide, sodium butoxide, potassium and sodium t-amyloxide, potassium hydroxide, sodium hydroxide, methyllithium, butyllithium, hexyllithium, phenyllithium, and tertiary alkylammonium hydroxides.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

It is the object of the present invention to provide an improved process for the synthesis of cyclopropylacetylene which is useful in the synthesis of benzoxazinones which are useful as HIV reverse transcriptase inhibitors. The methods of the present invention, by way of example and without limitation, may be further understood by reference to Scheme 1. Scheme 1 details the general synthetic method for synthesis of cyclopropylacetylene starting from cyclopropane carboxaldehyde and malonic acid. Alternatively, one skilled in the art of organic synthesis may react a malonic acid substitute, as described below, for malonic acid in Step (1) Similarly, alternative halogenating agents for halosuccinimide are described below.

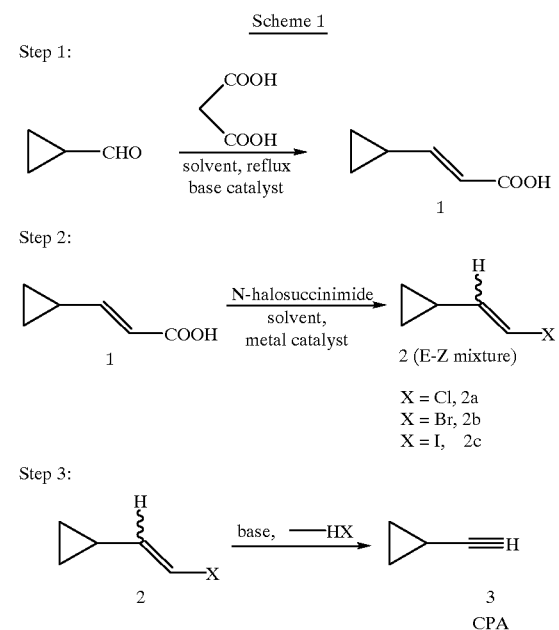

Step 1. Condensation: Preparation of cyclopropyl acrylic acid.

This step is conducted by reacting cyclopropane carboxaldehyde in a suitable nonaqueous solvent at a suitable temperature with malonic acid in the presence of a suitable base catalyst to form cyclopropyl acrylic acid. By way of general guidance, cyclopropane carboxaldehyde is contacted with about 1 to about 2 molar equivalents of malonic acid, stirred and heated, if necessary, to dissolve the reactants, additionally contacted with about 0.1 to about 5.0 mole equivalents of a suitable base catalyst and heated to a temperature sufficient to form cyclopropyl acrylic acid. During the formation of cyclopropyl acrylic acid, water is generated as a product and can be removed by standard methods in the art. Cyclopropyl acrylic acid may be separated from the reaction as a stable solid by standard methods of work up known to one skilled in the art of organic synthesis. Examples of standard work up are shown in Examples 1 and 2.

Suitable nonaqueous solvents are any hydrocarbon, ether, halogenated hydrocarbon, or aromatic solvents in which cyclopropane carboxaldehyde is soluble, and which, combined with the base used, give some solubility for malonic acid. These would include, but are not limited to, pentane, hexane, heptane, toluene, xylene(s), benzene, mesitylene(s), t-butylmethyl ether, dialkyl ethers (ethyl, butyl), diphenyl ether, chlorobenzene, methylene chloride, chloroform, carbon tetrachloride, acetonitrile, dichlorobenzene, dichloroethane, and trichloroethane. Preferred nonaqueous solvents are heptane, toluene and pyridine.

Suitable temperature for the condensation reaction is room temperature to refluxing temperature of the nonaqueous solvent, a condition readily determined by one skilled in the art of organic synthesis. It is preferred to run the reaction at refluxing temperature.

Preferred base catalysts are alkylamines and aromatic amines, especially pyridine, pyrrolidine, piperidine and morpholine or a combination thereof. Most preferred are piperidine or morpholine in combination with pyridine.

In an alternative to malonic acid a "malonic acid substitute" may be used. As used herein, examples of a malonic acid substitute, such as 2,2-dimethyl-1,3-dioxane-4,6-dione or suitable mono or bis esters of malonic acid, such as dimethyl or diethyl malonate or monomethyl malonate, might also be used. In the case of 2,2-dimethyl-1,3-dioxane-4,6-dione, much milder bases such as sodium acetate might be used to affect the condensation. Additional malonic acid substitutes such as cyano ethanoic acid, mono($C_1$–$C_6$)alkyl malonate, or di($C_1$–$C_6$)alkyl malonate might also be used to affect condensation. As used herein, "alkyl" is intended to include both branched and straight-chain saturated aliphatic hydrocarbon groups having the specified number of carbon atoms; for example, "$C_1$–$C_6$ alkyl" denotes alkyl having 1 to 6 carbon atoms, ie. methyl, ethyl, propyl, butyl, pentyl, hexyl, and branched isomers therein. Furthermore, it is understood by one skilled in the art of organic synthesis that the use of a malonic acid substitute in Step (1) may result in the formation of a protected cyclopropyl acrylic acid, such as a cyclopropyl acrylate ester. It is understood that such a product is readily converted by acid or base hydrolysis, methods known to one skilled in the art, to form the desired product, cyclopropyl acrylic acid.

It is understood that one skilled in the art can determine the preferred reaction time of Step 1 as dependent on temperature, base catalyst and nonaqueous solvent. Generally, the reaction time is about 1 to about 48 hours. The prefered reaction time is about 1 to about 12 hours.

Ste 2. Halogenation: Preparation of (E,Z)-1-halo-2-cyclopropylethylene.

This step comprises the halogenation of cyclopropyl acrylic acid by a halogenating agent in the presence of a metal catalyst. By way of general guidance, cyclopropyl acrylic acid and about 0.01 to about 0.5 molar equivalents, preferably 0.05 to 0.2 molar equivalents, more preferably 0.05 to 0.15 molar equivalents, most preferably about 0.1 molar equivalent of a metal catalyst is(are) dissolved in a suitable solvent after which about 1.0 to about 1.3 molar equivalents of a halogenating agent are added. The reaction is stirred for a sufficient amount of time, preferably about 2 minutes to about 48 hours, more preferably about 30 minutes to about 3 hours, depending on the catalyst, to form an E,Z mixture of 1-halo-2-cyclopropylethylene. (E,Z)-1-halo-2-cyclopropylethylene may be separated from the reaction as a stable liquid by distillation or by quenching with water followed by standard methods of work up. An example of standard work up is shown in Example 3.

Preferred metal catalysts for step (2) are lithium acetate, magnesium acetate, zinc acetate, calcium acetate, copper iodide, and copper bromide. Most preferred is lithium acetate.

Preferred halogenating agents for step (2) are N-chlorosuccinimide, N-bromosuccinimide, and N-iodosuccinimide; more preferred are N-chlorosuccinimide and N-bromosuccinimide; most preferred is N-bromosuccinimide.

Preferred solvents for step (2) are aqueous acetonitrile and aqueous acetone; most preferred is aqueous acetonitrile, 97:3 acetonitrile:water. In an aqueous solvent system the amount of water required is a sufficient amount of water to dissolve the metal catalyst and make a homogenous system.

Additionally, it is optional that the reaction of step (2) can be run in the presence of a phase transfer agent. Suitable phase transfer agents include Aliquat®336, crown ethers and tetra alkyl ammonium halide. Tetraoctyl ammonium chloride and tetrabutyl ammonium bromide are examples of suitable tetra alkyl ammonium halides.

Alternatively, step (2) may be conducted in organic solvents, for example saturated hydrocarbons, aromatic hydrocarbons, and ethers, in the presence of a phase transfer agent. Preferred organic solavents are anisole, xylene, and acetonitrile.

Step 3: Elimination: Preparation of cyclopropylacetylene.

This step comprises the elimination of hydrogen halide from 1-halo-2-cyclopropylethylene to form cyclopropylacetylene. By way of general guidance, a reaction vessel, fitted with a means for monitoring and controlling the reaction temperature, is charged with a suitable nonaqueous solvent and about 1 to about 3 equivalents of a strong base, depending on the base. It is preferred to use about 2 equivalents of a strong base. While agitating, 1-halo-2-cyclopropylethylene is added at such a rate that the internal temperature does not exceed the boiling point of cyclopropyl acetylene; preferably about 35° C. Upon addition, the reaction is stirred for about 10 minutes to about 24 hours, preferably about 10 minutes to about 4 hours, most preferably about one hour, at room temperature to form cyclopropyl acetylene. One skilled in the art can determine a suitable stirring time by the conditions and the reagents. The reaction is quenched with water or a mild acid, such as acetic acid. The cyclopropyl acetylene can then be isolated by distillation, vacuum distillation or atmospheric distillation. Vacuum distillation is preferred if the solvent has a high boiling point, for example dimethylsulfoxide. Atmospheric distillation can be used if the solvent has a low boiling point.

Nonaqueous solvents for step (3) are liquid ammonia, tetrahydrofuran, dimethylsulfoxide, N-methylpyrrolidinone, dimethylformamide, dioxane, diethyl ether, diphenyl ether, dibutyl ether, anisole, chlorobenzene, toluene, xylene(s), mesitylene, dodecane, and various mixed long-chain alkanes. A preferred solvent is dimethylsulfoxide. It is understood that suitable solvents for Step (3) do not react with the strong base added in Step (3).

Preferred 1-halo-2-cyclopropylethylenes are 1-bromo-2-cyclopropylethylene and 1-chloro-2-cyclopropylethylene.

Strong bases for step (3) are sodium amide, sodium methoxide, potassium t-butoxide, lithium diisopropylamide, sodium butoxide, potassium and sodium t-amyloxide, potassium hydroxide, sodium hydroxide, methyllithium, butyllithium, hexyllithium, phenyllithium, and tertiary alkylammonium hydroxides. Preferred bases are sodium amide, potassium hydroxide and potassium t-butoxide; more preferred are sodium amide and potassium t-butoxide; and even more preferred is potassium t-butoxide.

Additionally, it is optional that the reaction of step (3) can be run in the presence of a phase transfer agent. Suitable phase transfer agents include Aliquat®336, crown ethers, and tetrabutyl ammonium bromide.

The following examples are meant to be illustrative of the present invention. These examples are presented to exemplify the invention and are not to be construed as limiting the invention's scope.

EXAMPLE 1

Preparation of 3-Cyclopropyl Acrylic Acid (1):

Cyclopropane carboxaldehyde (100 g, 1.43 mol, 1 eq.) malonic acid (297 g, 2.85 mol, 2 eq.) and pyridine (565 g, 7.15 mol, 5 eq.) are stirred together in a suitable reaction vessel equipped with a reflux condenser and means of agitation. The suspension is stirred vigorously with warming to about 50° C. during which time the malonic acid gradually dissolves. Piperidine (15 ml, 15 mmol, 1 mol %) is then added and the reaction mixture is heated to 80–85° C. (internal temperature). After maintaining at this temperature for about 1.5 hours, the reaction mixture is heated so as to maintain at reflux (about 115° C.) for three hours. The reaction mixture is then cooled to 0° C., and 500 ml of cold water is added, followed by the slow addition of 680 ml of concentrated, aqueous, hydrochloric acid solution with vigorous stirring. A mass of pale yellow crystals gradually forms, which is removed by filtration and washed several times with cold water. This first crop of product is dried to a constant weight to yield 68 g (43%) of 3-cyclopropyl acrylic acid. The mother liquors are extracted with ethyl acetate (3×400 ml) and the combined organic layers are concentrated under vacuum to obtain a second crop of 28 g (17%) of product. The remaining mother liquors are then concentrated further and filtered once again to obtain 21 g (13%) of product. This represents an overall yield of 112 g (70%). The desired product has a melting point range of 63–65° C. (uncorrected) and gives satisfactory $^1$H NMR and mass spectra.

EXAMPLE 2

Preparation of 3-Cyclopropyl Acrylic Acid (1):

A solution of cyclopropane carboxaldehyde (7.0 g, 100 mmol) in 50 ml of toluene is treated with 11.5 g (110 mmol) of malonic acid. The stirred suspension is treated with 0.87 g (10 mmol, 10 mol %) of morpholine, followed by 3.95 g (50 mmol, 50 mol %) of pyridine. The mixture is then heated to reflux with provision made for the removal of water. Water is seen to separate from the reaction mixture for about one hour, during which time slightly more than the theoretical amount of water is removed (2 ml). The reaction mixture is now a clear, pale-yellow solution. The reaction is allowed to cool to ambient temperature, washed with 50 ml of 10% aqueous, hydrochloric acid solution, and washed twice with 50 ml portions of water. The toluene solution is concentrated to about one-quarter volume, diluted with 40 ml of n-heptane, and stirred with cooling to about 5° C. The product is seen to precipitate from solution as fine, pale-yellow needles. The product is collected by filtration and dried to a constant weight. The yield is approximately 8.5 g (76%). A second crop of product (1.7 g) can be obtained by evaporating the mother liquors to dryness under reduced pressure, followed by trituration of the resulting residue with cold (0° C.) n-heptane for a total yield of 10.2 g (91%).

EXAMPLE 3

Preparation of (E,Z)-1-bromo-2-cyclopropylethylene (2b)

The cyclopropyl acrylic acid obtained in Step 1 (30 g, 268 mmol, leq., made by Example 1) and lithium acetate dihydrate (2.73 g, 26.8 mmol, 0.1 eq) are dissolved in 300 ml of acetonitrile and water (9 ml). The solution is stirred at room temperature for about five minutes, and then is treated with N-bromosuccinimide (57.2 g, 321 mmol, 1.2 eq.). The reaction mixture is stirred at room temperature for 45 minutes; and then is quenched with 100 ml of H2O and extracted with hexanes (3×300 ml). The combined organic layers are dried over magnesium sulfate, filtered and concentrated under reduced pressure. The desired product is obtained as a mixture of stereochemical isomers as determined by $^1$H NMR and GC analysis (colorless liquid, 32 g, 82% yield; bp. 45° C./~20 mm Hg)

EXAMPLE 4

Preparation of Cyclopropylacetylene:

A suitable reaction flask equipped with a means of agitation and a means of monitoring temperature is charged with DMSO (20 ml) and potassium tert-butoxide (2.24 g, 20 mmol) to give a pale yellow solution. The cyclopropyl vinylbromide 2b (1.47 g, 10 mmol) is added at such a rate that the internal temperature does not exceed 35° C. The reaction is completed after stirring at room temperature for an additional 30 minutes after addition is complete. The reaction mixture is then treated with $H_{2O}$ (about 20 mmol, approximately 0.4 ml). The neat cyclopropyl acetylene is obtained by direct vacuum distillation from the reaction mixture in about 80% yield.

EXAMPLE 5

Preparation of 3-Cyclopropyl Acrylic Acid (1):

In a 3L four neck rounded flask equipped with a mechanical stirrer, an internal thermocouple and a Dean-Stark apparatus with a reflux condenser which is connected to a nitrogen inlet and an oil bubbler was charged with a solution of cyclopropyl carboxaldehyde (92%, 300 g (326 g), 4.28 mol, 1 eq.) in heptane (1.07 L). To this stirred solution was added malonic acid (534.1 g, 5.14 mol, 1.2 eq.) in one portion following by pyridine (173 ml, 2.14 mol, 0.5 eq.). The solution was vigorously stirred at 30° C. (may be warm up to 35° C. to help dissolution of malonic acid) for 15 minutes (to avoid lumps formation) and a catalytic amount of piperidine (42.33 ml, 0.1 eq, 0.428 mols) was carefully added. After addition was completed, the mixture was heated to 75° C. until it started refluxing. After two hours of refluxing the internal temperature was increased to 95° C. to keep a constant reflux for another two hours. The collected water from the Dean-Stark trap was 73 ml. The reaction was monitored by $^1$H-NMR indicating no aldehyde left after this period of time.

The reaction mixture is then cooled to 0° C., and an aqueous solution of HCl (670 ml, 0.8eq.) was slowly added to keep internal temperature below 10° C. A fine pale yellow precipitate was slowly formed. The heterogeneous mixture was stirred at 0° C. for 2 hours and then filtered through a 3000 ml fritter-glass buchner funnel. The solid cake was washed with a diluted aqueous solution of HCl (1×0.5N, 500 ml) and water (2×500 ml). The off-white solid was dried under air flow at room temperature overnight to afford 453 g (94%) of the cyclopropyl acrylic acid.

What is claimed is:

1. A process for synthesis of cyclopropylacetylene, said process comprising:

(1) contacting cyclopropane carboxaldehyde with malonic acid, or a malonic acid substitute, in the presence of a base catalyst to form 3-cyclopropylacrylic acid, (2) contacting 3-cyclopropylacrylic acid with a metal catalyst and a halogenating agent to form (E,Z)-1-halo-2-cyclopropylethylene; and (3) contacting (E,Z)-1-halo-2-cyclopropylethylene with a strong base to form cyclopropyl acetylene.

2. The process of claim 1 wherein the malonic acid substitute is selected from 2,2-dimethyl-1,3-dioxane-4,6-dione, dimethyl malonate, diethyl malonate, and monomethyl malonate.

3. The process of claim 1 wherein the base catalyst is selected from pyridine, pyrrolidine, piperidine, morpholine, N-methylmorpholine, 1,4-diazabicyclo[2.2.2]octane, N,N-dimethylaminopyridine, N,N-diethylaniline, quinoline, N,N-diisopropylethylamine, sodium hydroxide, potassium hydroxide, lithium hydroxide, cesium hydroxide, sodium carbonate, potassium carbonate, lithium carbonate, cesium carbonate, sodium alkoxide, lithium alkoxide and potassium alkoxide, wherein the alkoxide is selected from methoxide, ethoxide, butoxide, t-butoxide, and t-amyloxide.

4. The process of claim 1 wherein the metal catalyst is selected from lithium acetate, magnesium acetate, zinc acetate, calcium acetate, copper iodide and copper bromide.

5. The process of claim 1 wherein the halogenating agent is selected from N-chlorosuccinimide, N-bromosuccinimide, and N-iodosuccinimide.

6. The process of claim 1 comprising:

(1) contacting cyclopropane carboxaldehyde with malonic acid in the presence of a base catalyst selected from:
pyridine, pyrrolidine, piperidine, morpholine, N-methylmorpholine, 1,4-diazabicyclo[2.2.2] octane, N,N-dimethylaminopyridine, N, N-diethylaniline, quinoline, N,N-diisopropylethylamine, sodium hydroxide, potassium hydroxide, lithium hydroxide, cesium hydroxide, sodium carbonate, potassium carbonate, lithium carbonate, cesium carbonate, sodium alkoxide, lithium alkoxide and potassium alkoxide, wherein the alkoxide is selected from methoxide, ethoxide, butoxide, t-butoxide, and t-amyloxide;

to form 3-cyclopropylacrylic acid;

(2) contacting 3-cyclopropylacrylic acid with a metal catalyst selected from:
lithium acetate, magnesium acetate, zinc acetate, calcium acetate, copper iodide and copper bromide;

and a halogenating agent to form (E,Z)-1-halo-2-cyclopropylethylene; and (3) contacting (E,Z)-1-halo-2-cyclopropylethylene with methyllithium, potassium t-butoxide, potassium hydroxide, or sodium amide to form cyclopropyl acetylene.

7. The process of claim 6 comprising:

(1) contacting cyclopropane carboxaldehyde with malonic acid in the presence of a base catalyst selected from:
pyridine, pyrrolidine, piperidine, morpholine, or a combination thereof;

to form 3-cyclopropylacrylic acid;

(2) contacting 3-cyclopropylacrylic acid with a metal catalyst selected from:
lithium acetate, magnesium acetate, zinc acetate, calcium acetate, copper iodide and copper bromide;

and a halogenating agent to form (E,Z)-1-halo-2-cyclopropylethylene; and (3) contacting (E,Z)-1-halo-2-cyclopropylethylene with potassium t-butoxide, potassium hydroxide, or sodium amide to form cyclopropyl acetylene.

8. The process of claim 6 comprising:

(1) contacting cyclopropane carboxaldehyde with malonic acid in the presence of a base catalyst selected from:
pyridine, pyrrolidine, piperidine, morpholine, or a combination thereof;

to form 3-cyclopropylacrylic acid;

(2) contacting 3-cyclopropylacrylic acid with lithium acetate and a halogenating agent to form (E,Z)-1-halo-2-cyclopropylethylene; and (3) contacting (E,Z)-1-halo-2-cyclopropylethylene with methyllithium, potassium t-butoxide, potassium hydroxide, or sodium amide to form cyclopropyl acetylene.

9. The process of claim 1 further comprising in step (2) contacting 3-cyclopropylacrylic acid with a metal catalyst and a halogenating agent in the presence of a phase transfer agent to form (E,Z)-1-halo-2-cyclopropylethylene.

10. The process of claim 1 further comprising in step (3) contacting (E,Z)-1-halo-2-cyclopropylethylene with a strong base in the presence of a phase transfer agent to form cyclopropyl acetylene.

11. The process of claim 6 wherein the halogenating agent is N-bromosuccinimide.

12. The process of claim 7 wherein the halogenating agent is N-bromosuccinimide.

13. The process of claim 8 wherein the halogenating agent is N-bromosuccinimide.

* * * * *